United States Patent [19]

Wolfe et al.

[11] Patent Number: 5,232,848
[45] Date of Patent: Aug. 3, 1993

[54] BASAL NUTRIENT MEDIUM FOR CELL CULTURE

[75] Inventors: Richard A. Wolfe, Ellisville, Mo.; Aaron H. Heifetz, Columbia; Linda M. Custer, Ellicott City, both of Md.

[73] Assignee: W. R. Grace & Co.-Conn., New York, N.Y.

[21] Appl. No.: 437,955

[22] Filed: Nov. 16, 1989

Related U.S. Application Data

[63] Continuation-in-part of Ser. No. 29,577, Mar. 24, 1987, abandoned.

[51] Int. Cl.$^5$ ............................................. C12N 5/00
[52] U.S. Cl. ........................... 435/240.31; 435/240.1; 435/240.2; 435/240.3; 435/240.242
[58] Field of Search ............... 435/240.1, 240.2, 240.3, 435/240.31, 240.242

[56] References Cited

U.S. PATENT DOCUMENTS

| | | | |
|---|---|---|---|
| 3,450,598 | 6/1969 | Welsh et al. | 195/1.8 |
| 4,443,546 | 4/1984 | Stemerman et al. | 435/240 |
| 4,452,893 | 6/1964 | Ng et al. | 435/240 |
| 4,560,655 | 12/1985 | Baker | 435/240.31 |

OTHER PUBLICATIONS

Wolfe et al, BioTechniques, vol. 6, No. 1 (1988) pp. 62-65.
Heifetz et al, BioTechniques, (1989) vol. 7 pp. 192-199.
Bottenstein et al, Methods of Enzymology, vol. LVIII, ed. Jakoby and Pastan, "The Growth of Cells in Serum-Free Hormone-Supplemented Media" p. 109 (1979).
Freshney, Culture of Animal Cells: A Manual of Basic Technique, Chapter 9, pp. 67-78 (1983).
Leibovitz, Albert–"The Growth and Maintenance of Tissue-Cell Cultures in Free Gas Exchange With the Atmosphere"-AM. J. Hyg., vol. 78: 173-180 (1963) Good et al.
Iscove, N. N. et al.–"Complete Replacement of Serum by Alumin, Transterrin, and Soybean Lipid in Cultures of Lipopolysaccharide-Reactive B Lymphocytes"-J. Exp. Med., vol. 147: 923-933 (1978).
Ham, Richard G. et al.–"Media and Growth Requirements"-Meth. Enzym.-(1978).
Barnes, David et al.–"Methods for Growth of Cultured Cells in Serum-Free Medium"-Analyt. Biochem., vol. 102: 255-270 (1980).
Wolfe, Richard A. et al.–"Continuous Culture of Rat C6 Glioma in Serum-free Medium"-J. Cell Biol.-vol. 87: 434-441 (1980).
Barnes, David–"Serum-free Cell Culture: a Unifying Approach"-Cell-vol. 22: 649-655 (1980).
Ferguson, Wilfred J. et al.–"Hydrogen Ion Buffers for Biological Research"-Analyt. Biochem., vol. 104: 300-310 (1980).
Wolfe, Richard A. et al.–"Continuous Serum-free Culture of the N18TG-2 Neuroblastoma x Glioma Hybrid Cell Lines"-Cold Spring Harbor Conf., 9/1075-1088 (1982).
McHugh, Yvone E.–"Serum-Free Growth of Murine and Human Lymphoid and Hybridoma Cell Lines"-BioTechniques, 72-77 (1983).
Bering, Charles L.–"A Good Idea Leads to a Better Buffer"-J. of Chem. Education-vol. 64: 803-804 (1978).
KC Biological–"A Serum-Independent Medium for Maximum Performance in all Areas of Hybridome Technology"-Technical Information Bulletin 24.
KC Biological–"A Serum-Independent Medium for Immunological Applications"-Technical Information Bulletin 25.
Ventrex–"Completely Defined Serum Free Media'-'-(1984).
Bhattacharyya, Amitabha et al.–"Synthetic Organis pH Buffers can Support Fertilization of Guinea Pig Eggs, but not as Efficiently as Bicarbonate Buffer"-Gamete Research-19/123-129 (1988).

Primary Examiner—Douglas W. Robinson
Assistant Examiner—Susan M. Weber
Attorney, Agent, or Firm—Beverly K. Johnson

[57] ABSTRACT

This defined basal nutrient medium is very effective in both high and low density culture of a wide variety of cell lines and cell types. The medium may be used for serum-free culture or supplemented with low levels of serum. The medium contains a buffer system formulated for air equilibration.

14 Claims, No Drawings

BASAL NUTRIENT MEDIUM FOR CELL CULTURE

This application is a continuation-in-part of copending U.S. Pat. Ser. No. 029,577, filed Mar. 24, 1987.

BACKGROUND OF THE INVENTION

This invention relates generally to a medium for the in vitro culture of mammalian cells More specifically, the invention is a defined basal nutrient medium for serum-free culture or for culture when supplemented with low levels of serum. For serum-free culture, inorganic iron sources and/or defined proteins are added to the basal nutrient medium. The medium is very effective when used in either high or low density culture of a wide variety of cell lines and cell types.

For in vitro culture, a medium must, of course, supply all essential nutrients for the cells: vitamins, amino acids, lipids, nucleic acid precursors, carbohydrates, trace elements, and bulk ions. Historically, basal nutrient media were designed to support cell growth only after being supplemented with a biological fluid or extract, e.g., serum or other blood products (such as plasma, plasma proteins, hemoglobin) lipids, yeast extracts or embryo extracts. Serum, in particular, proved to be an effective supplement, presumably because it contains the necessary growth- and multiplication-promoting factors in physiologically acceptable concentrations. Examples of basal nutrient media of this type are Eagle's basal medium (BME), the composition of which is recited in U.S. Pat. No. 3,450,598 (Welsh et al.), and Dulbecco's Modified Eagle's (DME) medium, the composition of which is recited in Table II of Ham et al., "Media and Growth Requirements," *Methods of Enzymology*, (1978). DME medium, which contains relatively high concentrations of the essential amino acids and sugars, is representative of the commercially available media formulated for the mass culture of cells with serum supplementation.

With growing sophistication in cell culture techniques, factors present in serum or other biological extracts have been identified. It is now possible to grow mammalian cells in a serum-free environment, by supplementing a basal nutrient medium with defined proteins necessary for cell growth and multiplication. For example, Ham's F12 medium was formulated for clonal cell growth. F12, the composition of which is given in Table II of Ham et al., supra, contains low concentrations of the essential amino acids and sugars, but includes lipids, nucleic acid derivatives, vitamins and nonessential amino acids.

It is now generally accepted that a readily obtainable and sufficiently complex basal nutrient medium for mass culture of cells in low serum concentrations can be fabricated by mixing DME and F12 media. Such mixtures, when supplemented with the appropriate protein factors, can also support the serum-free growth of many cell types. Barnes et al., "Methods for Growth of Cultured Cells in Serum-Free Medium," *Analytical Biochem.*, Vol. 102, pp. 255-270 (1980), describes examples of both approaches.

Several commercially available nutrient media are based on mixtures of DME, F12 and/or other media such as those listed in Table II of Ham et al., supra. However, simple mixtures of existing commercial media are by no means optimal for culturing all cell lines and medium preparations therefore have been targeted largely to particular cell lines or cell types. Wolfe et al., "Continuous Culture of Rat C6 Glioma in Serum-Free Medium," *J. Cell Biol.*, Vol. 87, pp. 434-41 (1980), teaches the use of a 3:1 DME-to-F12 mixture, supplemented with trace elements, and further supplemented with the following defined proteins: insulin, transferrin, fibroblast growth factor, linoleic acid complexed to fatty acid-free bovine serum albumin, and serum-spreading factor (vitronectin).

With the increasing use of cultured mammalian cells to produce biologicals (e.g., monoclonal antibodies and genetically engineered proteins), there is an increasing demand for chemically defined, serum-free media. Purification of the desired cellular product is greatly complicated by the presence of serum, which may contain at least several hundred different proteins. It is therefore desired to reduce the protein content of the culture medium to a few defined compounds from which the monoclonal antibody or other cellular product can be separated more readily. Defined protein includes any specific, identifiable, purified protein. Defined proteins include, but are not limited to, albumin, transferrin, insulin, vitronectin, fibroblast growth factor, insulin-like growth factor, laminin, fibronectin and its derivatives, and other hormones, growth and attachment factors.

In addition to necessary nutrients and protein factors, the medium must have a means for controlling pH levels. Most typically, pH control relies on a bicarbonate/carbon dioxide buffer system, which requires carbon dioxide regulators as well as incubators which supply a constant level of carbon dioxide to the culture. The buffering capacity of the system can be expanded by the inclusion of a biocompatible organic buffer, such as alpha-glycerolphosphate or HEPES (N-2-hydroxyethylpiperazine-N'-2-ethanesulfonic acid) or other zwitterionic buffers. Alternatives to the cumbersome bicarbonate/carbon dioxide buffer system have been proposed, but have not received significant acceptance in the field. See, for example, Leibovitz, "The Growth and Maintenance of Tissue-Cell Cultures in Free Gas Exchange with the Atmosphere," *Am. J. Hygiene*, Vol. 78, pp. 173-80 (1963), disclosing a medium (L-15) which uses free base amino acids and substitutes D(+)galactose, sodium pyruvate and DL-alpha-alanine for glucose. It is taught that the L-15 medium can be used in free gas exchange with the atmosphere. Ferguson, et al. (*Analyt. Biochem* (1980) 04:300-310) describe using zwitterionic buffers in mammalian tissue culture However, in every case the media was also supplemented with 10% serum, incubated in air containing 5% $CO_2$, and supported cells only at low density. Bhattacharyya et al. (*Gamete Research* (1988) 19:123-129) used synthetic organic buffers in culture medium as a replacement for bicarbonate/carbon dioxide. Their research indicated that bicarbonate/carbon dioxide is far better in supporting the production and growth of embryos in in vitro fertilization than any of the synthetic organic buffers. To date, no media have been formulated specifically to support growth at high and low cell densities in the absence of serum and carbon dioxide incubation.

SUMMARY OF THE INVENTION

The basal nutrient medium of the present invention is designed for high or low density mammalian cell culture when supplemented with defined protein factors, inorganic iron supplements, or very low levels of serum. The medium contains a buffer system which utilizes air equilibration.

The primary objective of this invention is to provide a chemically defined medium which is advantageous for high density culture of mammalian cells and which supports such culture in the absence of serum or in the presence of very low serum concentrations. One important intended benefit is reduction of the concentrations of growth inhibitors that are present in serum. In addition, by providing a culture medium with low levels of exogenous protein, recovery and purification of the desired cell product will be facilitated.

One embodiment of the invention replaces the defined protein iron-saturated transferrin with inorganic iron supplements, such as ferric sulfate, ferric citrate, ferrous fumarate, or ferrous ammonium sulfate. This is especially advantageous, since the inorganic iron supplement is less expensive than transferrin, and also the purification is simplified due to lower amounts of extraneous protein.

A more specific object is to design a medium having a sodium/potassium ratio and a total osmolarity compatible with high levels of immunoglobulin production by hybridoma cells. It is also intended that the medium be free of polypeptides which co-purify with immunoglobulins. It is a goal of this invention to markedly improve the purity of the cellular product recovered from the culture.

It is an additional goal to provide a cell culture medium particularly well suited for use in hollow fiber bioreactors. To achieve this goal, it is intended that the medium formulation be capable of avoiding or reducing changes in osmolarity sufficient to have a deleterious effect on the cultured cells.

It is a further object to design a medium having nutrients at levels which are suitable for high cell densities, but which are not inhibitory for low density culture. It is intended to eliminate the need for media changes when going from low to high density culture conditions, as well as to reduce or eliminate the need for "weaning" cells from serum-supplemented to serum-free media.

Still another object of the invention is to design a basal nutrient medium which is suitable for the culture of a wide variety of cell types and sources. It is intended that this medium be compatible with the clonal growth of human cells.

Yet another important object is to provide a medium with a buffer system that is formulated for equilibration with air, rather than with mixtures of air and carbon dioxide.

One embodiment of the invention is a basal nutrient medium which does not contain D-glucose as a carbohydrate source. This embodiment can be used as a research tool in the field of artificial pancreas research or fields which need to specifically vary the level of glucose used. This can be used as a means to modify lactate production and thus stabilize pH. In this field it is important not to have exogenous glucose around to interfere with experiments in which varying levels of glucose will elicit insulin production. This embodiment also allows for unique formulations with other carbohydrate sources, such as fructose, galactose, mannose, lactose, sucrose, etc., which may be better suited for a particular type of fermentation or cell type. This embodiment also can be mixed with other glucose-containing media or supplemented with glucose to meet unique fermentation or cell type requirements.

BRIEF DESCRIPTION OF THE TABLE

TABLE 1 is a listing of the components of the medium of this invention, including the molecular weight and the concentration of each component.

DETAILED DESCRIPTION OF THE INVENTION

The basal nutrient medium described herein is a completely new formulation of nutrients and other components which is suitable for both high and low cell density culture. The medium comprises appropriate levels of essential and non-essential aminoacids and amino acid derivatives, bulk ions and trace elements, buffers, vitamins, coenzymes, carbohydrates and derivatives, nucleic acid derivatives, and lipids to function as an all-purpose nutrient medium for in vitro mammalian cell culture. The basal medium is designed to be supplemented either with defined proteins, inorganic iron sources or with low levels of serum or other biological extracts. The buffer system of this medium is specially formulated to allow for air-equilibrated pH control.

It is typical for nutrient media to be individually designed for specific uses or for the growth of particular cell lines or cell types. Prior art formulations useful for high cell densities frequently have been found to contain high concentrations of certain components that are grossly inhibitory for low cell density culture. In addition, many prior media have been specifically formulated for growth of one cell line and contain components whose concentrations have been optimized for that cell line only. No prior art medium or combination of media contains all of the components of the presently described media, nor are individual components used in the same concentrations as in any prior art media.

The medium described herein is an all-purpose basal nutrient medium. It has been demonstrated to effectively support both low and high density cell culture. It has been demonstrated to supply the nutrients needed by a variety of cell lines and types including murine, human or other hybridomas, hepatocyte lines, such as HepG2, UMR 108, fibroblast lines, such as 3T3 and 3T12, and Chinese Hamster Ovary cells. The medium is particularly well-suited for production of monoclonal antibodies in a variety of production modes, such as hollow fiber bioreactors, fermenters, spinner flasks and roller bottles. Where the medium is supplemented with defined proteins (i.e., hormones and growth factors), inorganic iron sources or with low levels of serum, high purity cell products, e.g., monoclonal antibodies and recombinant proteins are readily recoverable.

Most of the major nutrients and other factors essential for cell growth are known and have been used previously in many combinations and permutations. The concentrations of the components, however, have been newly formulated for the nutrient medium of this invention. The components have not merely been optimized for one particular cell line or set of production conditions, as is commonly done in this industry. Rather, the components have been optimized as an interrelated set of growth factors and enhancers in an all-purpose culture medium. In addition, the pH control system differs dramatically from prior art media.

The components described herein and listed in TABLE 1 are given in the physical and ionization states common in the art of media preparation. However, other physical and/or ionization states may be used, if desired. The concentration of any of the components, with the exception of the zwitterionic buffer and sodium hydroxide, may be varied from that listed in TABLE 1 by as much as a factor of two as long as the osmolarity, pH and sodium-to-potassium ratio are within the ranges described herein. The zwitterionic buffer concentration can range from about 10.0 to about 50.0 mM, preferably about 25.0 mM. The quantity of NaOH used is a function of the pH selected Bulk Ions and Trace Elements—Bulk ions are necessary for cell growth and for maintenance of membrane potentials and osmotic balance. They also play co-factor roles in enzymatic reactions. Sodium, potassium, calcium, magnesium, chloride, phosphate, and sulphate all perform important functions in normal cell metabolism. The specific sodium-to-potassium ratio in the medium, important in regulating transmembrane potential, is discussed further below. Bicarbonate or carbon dioxide is also necessary, and must be provided in the culture medium for low density cell culture. In high density cell culture, the cells themselves may generate sufficient levels, without the need for exogenous bicarbonate and carbon dioxide. Trace inorganic elements (iron, zinc, selenium, silicon, vanadium, copper, nickel and molybdenum) are necessary for the function of many enzymes (e.g., $Se^{++}$ in glutathione reductase). Trace inorganic elements also can directly modulate transmembrane signaling events (e.g., vanadate modulation of insulin responsiveness). Trace metals, in general, are not commonly used in serum free media. The specific compounds listed in TABLE 1 are commonly used in media preparations and are preferred because the indicated hydration states are advantageous for the stability of the powdered form of the medium of this invention. Substitutions may be made by those of ordinary skill in the art.

Amino Acids—The following amino acids are included in this medium: L-arginine (L-Arg), L-cysteine (L-Cys), L-glutamine (L-Gln), L-histidine (L-His), L-hydroxyproline (L-Hydroxy-Pro), L-isoleucine (L-Ile), L-leucine (L-Leu), L-lysine (L-Lys), L-methionine (L-Met), L-phenylalanine (L-Phe), L-threonine (L-Thr), L-tryptophan (L-Trp), L-tyrosine (L-Tyr), L-valine (L-Val) L-alanine (L-Ala), L-asparagine (L-Asn), L-aspartic acid (L-Asp), L-glutamic acid (L-Glu), glycine (Gly), L-proline (L-Pro) and L-serine (L-Ser). In addition, the amino acid derivatives glutathione and putrescine are present in the medium of this invention. Again, the forms listed in TABLE 1 are preferred, particularly for the preparation of a powdered medium that will dissolve readily However, alternative forms of these amino acids may be selected.

Vitamins/Coenzymes—A number of water soluble vitamins and co-enzymes are known to aid cell culture. Biotin, pantothenic acid, folic acid, folinic acid, niacinamide (nicotinamide), p-aminobenzoic acid, pyridoxal, pyridoxine, riboflavin, thiamine and vitamin $B_{12}$ are utilized in this medium.

Carbohydrates—Glucose, pyruvate and glutamine are utilized as the energy and carbon sources in the present medium. Pyruvate is provided as sodium pyruvate It may be desired for process control to alter the components used by the cells as an energy source For example, the glucose may be replaced by galactose or fructose, and the glutamine concentration varied. In one embodiment of the invention, glucose is left out entirely This medium allows for alternative energy sources to be used. This medium can also be used as a research tool in the development of artificial pancreas devices and experimental systems requiring the exogenous addition of specific glucose levels, e.g., glucose transport studies.

Nucleic Acid Derivatives—Adenine and hypoxanthine are provided as sources of purines. Thymidine is provided as a source of pyrimidines.

Lipids—The formulation of this invention includes the following lipids, lipid precursors and lipid derivatives: choline, ethanolamine, i-inositol, linoleic acid and lipoic acid. Additional lipids and other derivatives such as methyl lineolate may be added or substituted as required for particular cell types. Ethanolamine is a major component in the membrane phospholipid biosynthetic pathway.

Buffers—The buffer system of the nutrient medium described herein is unique. This system offers the operator the ease and flexibility of using air equilibration for pH control. This is an important aspect of the present invention, since the medium is primarily intended for serum-free or very low serum concentration culture. It has been found that when the serum concentration is reduced, the levels of bicarbonate normally suitable for pH control in equilibrium with 10% carbon dioxide/air become inhibitory. The present buffer system also offers an alternative to the burdensome adjustment of carbon dioxide concentrations which previously have been required for maintaining the pH within physiologically compatible ranges.

The buffer system utilizes sodium bicarbonate, sodium hydroxide, carbon dioxide and zwitterionic buffers. Zwitterionic buffers were first described by Good et al., (*Biochemistry* (1966) 5:467). Zwitterionic buffers include, but are not limited to, HEPES (N-2-hydroxyethyl piperazine-N'-2-ethanesulfonic acid), MOPSO (3-[N-morpholino]-2-hydroxy propanesulfonic acid), BES (N,N-bis(2-hydroxyethyl)-2-aminoethane sulfonic acid), and TAPSO (3-[N-tris(hydroxymethyl)methylamino]-2-hydroxy propanesulfonic acid). Zwitterionic buffers may be used individually or in combination such that the final concentration is between about 10 mM and about 50 mM, preferably about 25 mM. The small quantities of carbon dioxide required for cellular metabolism in low density cultures are provided in the medium of this invention via equilibration of atmospheric carbon dioxide and the $HCO_3^-$ present in the medium. For high density cultures, sufficient carbon dioxide is produced via normal cell metabolism. Particularly in the case of hollow fiber bioreactors, which have very densely packed beds of functioning cells, large quantities of carbon dioxide are generated. If the buffering system is based on carbon dioxide/bicarbonate equilibrium, the environment can rapidly become too acidic for the cells to function at optimal levels The air-equilibrated buffer system in the present medium eliminates this problem.

The need for using the pH indicator phenol red is eliminated in the medium of this invention, since the buffer system of this medium will maintain the pH within physiological ranges under common culture conditions in an air-equilibrated system. This is extremely advantageous in terms of purifying the desired cellular product, since phenol red binds to proteins, changing their chromatographic behavior. In addition, phenol red may affect cellular biosynthesis and metabolism. Elimination of phenol red is therefore significant in terms of reducing the required purification steps and increasing recoverable product The medium may be formulated at about pH 7.0 to about pH 7.4 at 37° C. Formulation at a higher pH, for example, at about pH 8.0, may be employed as a process control strategy for continuously fed bioreactors to neutralize the lactic acid produced by the cultured cells, instead of adding additional base as a process control strategy When the medium is to be used in a hollow fiber bioreactor, formulation at about pH 7.35 to about pH 7.8 (37° C.) is preferred. A pH of 7.2 (37° C.) is preferred for other uses.

Use of the zwitterionic buffers in high density culture is especially desirable. Optimal process pH varies depending on cell line, etc. The pKa (37° C.) values of the zwitterionic buffers HEPES, MOPSO, BES, and TAPSO are 7.3, 6.75, 6.9 and 7.4 respectively. A specific buffering system can be engineered to meet various cell needs using zwitterionic buffers. For hybridomas, the media is formulated at about pH 7.35 (37° C.), the process pH at high density is often about pH 6.8 (37° C.) and zwitterionic buffers have better buffering capacity due to optimal pKa values in that range. Other cell lines may need to be maintained above pH 7 or pH 7.2; therefore, the ability to switch to a buffer with a higher pKa (e.g., TAPSO) is very valuable Osmolarity—The sodium/potassium ratio and total osmolarity of the medium have been adjusted for compatibility with high levels of murine immunoglobulin production or other recombinant protein production The preferred sodium-to-potassium ratio is about 30, but may range from about 25 to about 35. The osmolarity of the medium is low, about 285 to about 315 mosm, preferably about 295 to about 305 mosm.

The medium described herein is particularly well suited for the production of monoclonal antibodies in hollow fiber bioreactors, fermenters, spinner flasks and roller bottles The high levels of gas exchange routinely employed in these types of culture are compatible with the present formulation. The osmolarity of the medium has been kept low to allow for some rise during culture, while still maintaining the osmolarity within ranges suitable for maintaining healthy, productive cells. For use in hollow fiber reactors, the medium preferably is reconstituted at about 295 mosm. In addition, biocompatible reducing agents, such as glutathione have been included in the medium to compensate for potential oxidative complications arising from these high levels of gas exchange.

The formulation for the basal nutrient medium of this invention is listed in TABLE 1. Quantities of the components are given in molarity as well as concentration. The formulation of TABLE 1 is the preferred embodiment of this invention. The quantity of each component may be varied by a factor of 2, that is, the quantity of each component may vary from about 50% to about 200% of the quantity listed in TABLE 1. The concentrations for each component have been selected on the basis of the mechanism by which it enters the cell, i.e., active or passive transport, and the concentrations required to achieve sufficient transport for the desired level of biological activity.

The hydration state of the individual components and the prepared basal nutrient medium may be varied according to convenience The hydration states given herein are those which are commonly used in the art of media preparation. However, as a practical matter, it is preferred to have the prepared medium be as dry as possible.

The basal nutrient medium as described above may be formulated and packaged as a dry or concentrated preparation for reconstitution prior to use. In the preferred embodiment of this invention, the medium is prepared as a dry powder, comprising the first sixty components listed in TABLE 1. The remaining two components are then added when the dry medium is reconstituted. Reconstitution may be done just prior to use. Alternatively, the medium may be reconstituted and packaged The shelf life of this medium as a dry powder stored at about 4° C. is at least several years. The liquid medium, either as prepared or as reconstituted from the dry powder is less stable, but when stored at about 4° C. is stable for about two months to six months or more.

Reconstitution may be performed by adding concentrated stocks of bicarbonate, base or other of the medium components, so long as the relative concentrations described above and indicated in TABLE 1 are present. If those components are added as solids, reconstitution is accomplished by the addition of sterile, de-ionized tissue culture grade water The medium is sterilized prior to use. A protocol for reconstituting the powdered medium is detailed in Example I.

Additional antioxidants, reducing agents, vitamins, carbohydrates, amino acids and/or derivatives, nucleic acids and/or derivatives, and proteins may be added prior to, during or after reconstitution. The principal added components will be proteins and/or other hormones.

As stated above, the basal nutrient medium of this invention is designed to be supplemented either with low levels of serum or with defined proteins The medium will support cell growth and metabolism when supplemented with amounts of serum appropriate for the particular cell line being cultured However, it has been demonstrated that considerably lower levels of serum are required to supplement the medium of this invention than are typically used with the prior art media. This formulation may be used serum-free or with very low levels of serum, preferably less than about one percent by volume, although higher levels may be used if desired.

The medium described herein can be used for serum-free cell culture when supplemented with a minimum number of defined proteins The precise protein supplement will depend on the needs of the cells being cultured. The preferred protein supplement for murine hybridomas consists of insulin and albumin; an iron source is also preferred. Insulin may be present in concentrations of about 1.0 to about 10.0 $\mu$gm/ml, preferably about 5.0 $\mu$gm/ml. Albumin may be present in concentrations of about 10.0 to about 1000.0 $\mu$gm/ml, preferably about 50.0 $\mu$gm/ml. Iron-saturated transferrin may be used if needed as the iron source in concentrations of about 0.1 to about 25.0 $\mu$gm/ml, preferably about 10.0 $\mu$gm/ml. Supplementing the basal nutrient medium with these proteins has been found to be excellent for both high and low density cell culture. Inorganic iron supplements, such as ferric sulfate and ferric citrate can be used to exhibit the properties of iron-saturated transferrin. The inorganic iron supplements may be present in concentrations of about 1 $\mu$M to about 50 $\mu$M. Additional proteins may be added if desired.

The examples which follow are given for illustrative purposes and are not meant to limit the invention described herein. The following abbreviations have been used throughout in describing the invention:

| | |
|---|---|
| BSA | bovine serum albumin |

| | -continued |
|---|---|
| °C. | degree(s) Centigrade |
| cm² | cubic centimeter(s) |
| DME | Dulbecco's Modified Eagle's |
| FBS | fetal bovine serum |
| gm | gram(s) |
| L | liter(s) |
| μ | micro- |
| mM | millimolar |
| mg | milligram(s) |
| min | minute(s) |
| ml | milliliter |
| mosm | milliosmolality (μmol/Kg) |
| M | molar |
| MW | molecular weight |
| N | normal |
| nm | nanometer(s) |
| osm | osmolality (mmol/Kg) |
| PBS | phosphate buffered saline |
| % | percent |
| rpm | revolution(s) per minute |
| TF | transferrin |
| v | volume |
| wt | weight |

EXAMPLE I

Preparation of Medium

Powdered Medium—The medium was prepared by mixing the first sixty components listed in TABLE 1 (that is, all components with the exception of $NaHCO_3$ and NaOH) in the quantities listed in TABLE 1. The ingredients are milled to form a dry powder. Unless specifically stated, the zwitterionic buffer is assumed to be 25 mM HEPES in the following examples.

Bicarbonate/Base Stock Solutions—Biocarbonate/Base ($NaHCO_3$/NaOH) stock solutions were prepared as follows:

(1) For pH 7.2 (37° C.), the stock was prepared by adding 17.922 gm NaHCO to 711.2 ml of a 1.00 N solution of NaOH The volume was then adjusted to 20 one liter.

(2) For pH 7.35 (37° C.) hollow fiber bioreactor medium, the stock was prepared by adding 17.922 gm $NaHCO_3$ to 950.0 ml of a 1.00 N solution of NaOH. The volume was then adjusted to one liter.

Reconstitution of Powdered Medium—Six liters of tissue culture grade water were placed in a 10.0 liter vessel, to which a 195.7 gm quantity of the powdered medium (a ten liter-equivalent package) was added. The package was rinsed twice with 100.0 ml aliquots of water. Next, 150.0 ml (15.0 ml/L of medium) of the bicarbonate/base stock solution was added to the vessel. The appropriate bicarbonate/base stock solution was selected, depending on the use to which the medium would be put. The sides of the vessel were rinsed with 630.0 ml water to insure that all the powder dissolved. The volume was brought to 10.0 L with water.

The pH of the standard reconstituted medium was determined (at 37° C.) to be 7.18±0.03 with a blood gas analyzer (Corning). The pH of the bioreactor reconstituted medium was determined to be 7.35±0.03 (37° C.). The osmolarity was determined to be 295±5.0 mosm by vapor pressure osmometry (Wescor)

The reconstituted medium was filter sterilized using a Masterflex TM pump (#25 head) (Cole-Parmer) at approximately 500.0 ml/min. The solution was passed through a Milli-stack GS (TM) filter (Millipore MSG-SO5C22) into sterile glass or polycarbonate carboys.

The reconstituted medium was tested to verify sterility and ability to promote cell proliferation. A 10.0 ml aliquot of medium supplemented with Protein Supplement A:

| |
|---|
| 50.0 μgm/ml bovine serum albumin (ICN Biologicals), |
| 1.0 μgm/ml iron-saturated human transferrin (ICN Biologicals), |
| 5.0 μgm/ml bovine insulin (Sigma Chemical Co.) |

The aliquot was sterilely placed in a tissue culture flask (T-75) to which one million CRL 1606 murine hybridoma cells (obtained from the American Type Culture Collection (ATCC.), 12301 Parklawn Drive, Rockville, Md. 20852) were added. The flask was tightly clasped and incubated at 37° C. for 24 hours. A 100 μL aliquot then was diluted with 10.0 ml PBS and the cell concentration determined using a Coulter Counter (TM) particle counter (Coulter Electronics). At least 200,000 cells/ml were observed, indicating the ability of the medium to support the culture.

The bottled medium was left at room temperature overnight to verify sterility. No cloudiness or other evidence of microbial contamination was observed The medium was then stored at 4° C.

EXAMPLE II

This example compares cell growth and monoclonal antibody production in the serum-free medium of Example I supplemented with Protein Supplement A versus serum-supplemented DME (Dulbecco's Modified Eagle's) medium. Better cell growth and antibody production were seen with the medium of this invention.

An aliquot of cells of the murine hybridoma line CRL 1606 was inoculated as shown in Table II into the reconstituted medium of Example I (pH 7.2). This was designated Culture IIA. Another aliquot of cells was inoculated into DME medium (GIBCO/BRL) supplemented with 10% (v/v) fetal bovine serum (GIBCO/BRL) This was designated Culture IIB. The media and cells were placed in polystyrene roller bottles (Corning, 490 cm²). The bottle containing Culture IIA was tightly sealed. The bottle containing Culture IIB was gassed with 10% carbon dioxide/air prior to sealing. Both bottles were placed in an incubator at 37° C. on a roller apparatus at about 1.0 rpm.

Aliquots of each culture were removed daily and the cell concentrations were determined with a Coulter Counter (TM) particle counter (Coulter Electronics). Cell viability was determined by the trypan blue dye exclusion assay (Sigma Chemical Co.) The results are shown in Table II.

The cells were removed from each daily aliquot by centrifugation. The conditioned medium supernatant from each aliquot was stored at 4° C. until termination of the experiment. The antibody (anti-fibronectin IgG) present in each aliquot was determined by ELISA analysis

TABLE II

| | Viable Cells (billions/L) | | Antibody (mg/L) | |
|---|---|---|---|---|
| Hour | IIA | IIB | IIA | IIB |
| 0 | 0.021 ± .001 | 0.022 ± .001 | — | — |
| 25 | 0.040 ± .001 | 0.021 ± .001 | — | — |
| 47 | 0.098 ± .001 | 0.059 ± .001 | 3.2 | 2.2 |
| 71 | 0.310 ± .017 | 0.185 ± .005 | 8.1 | 4.5 |
| 97 | 1.200 ± .016 | 0.740 ± .026 | 16.6 | 11.5 |
| 120 | 2.300 ± .030 | 2.000 ± .028 | 80.3 | 100.0 |
| 144 | 0.910 ± .018 | 1.500 ± .010 | 262.9 | 149.6 |
| | | | 307.8 | 238.6 |

TABLE II-continued

| Hour | Viable Cells (billions/L) | | Antibody (mg/L) | |
|------|------|------|------|------|
|      | IIA  | IIB  | IIA  | IIB  |
| 169  | —    | —    | 1000.0 | 420.0 |

EXAMPLE III

This example compares cell growth and antibody production in the medium of this invention versus another serum-free medium, both supplemented with the same defined proteins As in Example II. CRL 1606 cells were inoculated as shown in Table III (Hour 0) into roller bottles containing either the medium of this invention (Culture IIIA) or medium prepared from commercially available preparations (Culture IIIB). Culture IIIA was prepared by inoculating with the medium of Example I (pH 7.2) supplemented with Protein Supplement A. Culture IIIB was prepared by mixing 3 parts DME medium (GIBCO/BRL) with 1 part F12 medium (GIBCO/BRL), 25 mM HEPES (Sigma Chemical Co.), 0.02 mM ethanolaxine (Sigma Chemical Co ) and 3.0 mM sodium bicarbonate (Sigma Chemical Co.), and supplementing with Protein Supplement A. The pH of both preparations was adjusted with sodium hydroxide until the value approached 7.2 at 37° C. according to a Corning blood-gas analyzer. The osmolarity of both formulations was adjusted to approximately 295 mosm according to a Wescor vapor-pressure osmometer The procedures of Example I were repeated. The results are shown in Table III.

TABLE III

| Hour | Viable Cells (billions/L) | | Antibody (mg/L) | |
|------|------|------|------|------|
|      | IIIA | IIIB | IIIA | IIIB |
| 0    | 0.050 ± .001 | 0.049 ± .001 | —    | —    |
| 21   | 0.094 ± .004 | 0.086 ± .004 | 9.4  | 12.5 |
| 46   | 0.360 ± .009 | 0.290 ± .006 | 20.1 | 21.0 |
| 71   | 1.100 ± .003 | 0.700 ± .010 | 73.6 | 72.5 |
| 93   | 2.000 ± .032 | 1.400 ± .014 | 209.7 | 132.0 |
| 117  | 0.630 ± .012 | 1.100 ± .004 | 452.3 | 136.2 |
| 140  | —    | 0.440 ± .019 | 457.0 | 231.0 |
| 165  | —    | —    | 792.0 | 165.0 |

EXAMPLE IV

This example compares the purity of monoclonal antibody produced in cultures based on media of this invention versus that produced in cultures based on serum-supplemented media.

Two roller bottles were inoculated with $2.1 \pm 0.1 \times 10^4$ CRL 1606 cells per milliliter of medium. One bottle (Culture IVA) contained the medium of Example I (pH 7.2) supplemented with Protein Supplement A. The other bottle (Culture IVB) contained DME medium supplemented with 10% (v/v) fetal bovine serum. Samples of the conditioned medium were prepared as described in Example II after one and four days of culture The proteins contained in the samples were then examined by high performance size exclusion chromatography (HPSEC, Zorbax (TM) (E. I. duPont de Nemours Co.) 0.75×25 mm column isocratic 0.3M sodium chloride/0.05M sodium phosphate; pH 7.0; 0.25 ml/min).

Table IV presents the relative amounts of materials migrating with retention times similar to standards of highly purified BSA (bovine serum albumin) or IgG (immunoglobulin G). Absorbance at 280 nm was measured, and the integrated peak areas determined. In addition, it is shown that the monoclonal antibody produced in Culture IVB was undetectable amongst the bovine IgG and albumin (3.2±0.35 mg/ml total IgG and albumin) present by virtue of the 10% fetal bovine serum supplement.

TABLE IV

| Sample | Peak Area Units | |
|--------|------|------|
|        | IgG (Rf = 16.7) | BSA (Rf = 17.7) |
| IVA. Day 1 | Baseline | 5,770 (Rf = 17.63) |
| IVA. Day 4 | 15,647 (Rf = 16.75) | 5,470 (Rf = 17.95) |
| IVB. Day 1 | Buried | 686.528 (Rf = 17.63) |
| IVB. Day 4 | Buried | 641.592 (Rf = 17.92) |

At 280 nm, the absorbance of a 1.0 gm/ml solution of IgG is 1.715 times that of a solution of 1.0 mg/ml BSA. Thus, the data in Table IV suggests that the Culture IVA, Day 4 sample contained approximately 170 µgm/ml IgG and that the monoclonal antibody was about 63% pure:

$$\frac{[IgG]}{[BSA] + [IgG]} = \frac{1.668 \times [BSA]}{[BSA] + (1.668 \times [BSA])}$$

$$= \frac{1.668 \times [BSA]}{(1 + 1.668) \times [BSA]}$$

$$= \frac{1.668}{1 + 1.668}$$

$$= 0.63 = 63\%$$

where:

$$[IgG] = \frac{A_{280}IgG \, 1.715}{A_{280}BSA} \times [BSA]$$

$$= 1.668 \times [BSA]$$

In addition, it appears that highly purified IgG can be obtained after only a simple size exclusion chromatographic step. Crude conditioned medium of both higher product titer and greater product purity can easily be obtained by culturing the cells for a few more days. Under the conditions of this example, the cells in Culture IVA had only reached a density of 1,000,000 cells/ml by Day 4, which is less than half the saturation density.

EXAMPLE V

This example demonstrates the utility of this medium for reviving cells from cryopreservation. The example also demonstrates that the described medium can support the proliferation of cells which previously have been cultured in the presence of high serum concentrations, without the need for prior adaptation ("weaning") procedures.

Cells of the HB127 cell line (SP2/0 Ag14) were obtained from ATCC. This cell line had always been grown in serum-supplemented media. This SP2/0 murine hybridoma line was derived from a different parental fusion partner than the CRL 1606 line used in Examples I–IV. These two cell lines together are representative of most of the monoclonal antibody producing cells commonly used in the industry. The examples demonstrate that both grow better in the medium of this invention than in serum-supplemented DME medium.

The cells were thawed and divided into two equal portions. The portions were incubated overnight at 37° C. in 5.0 ml of either the reconstituted medium of Example I (pH 7.2), supplemented with Protein Supplement A (Culture VA) or in DME medium supplemented with 10% serum (Culture VB). On day 2, the medium in each culture was exchanged via centrifugation with a fresh preparation. The cultures were returned to the incubator. On day 5, the cells in each culture were counted. In Culture VA, 687,000 cells/ml were observed, versus only 251,000 cells/ml in Culture VB. Therefore, even this cell line which had always been grown in serum-supplemented media grew significantly better in the serum-free medium of this invention, without any intermediate weaning cultures being necessary.

EXAMPLE VI

This example demonstrates the suitability of this medium for the culture of anchorage dependent cell lines in the presence of low concentrations of serum. Cell lines were examined from two different species and two different tissues.

For this experiment, LLC-PK1 (porcine kidney) cells (ATCC number CL101) and CPAE (bovine endothelial) cells (ATCC number CCL 209) were obtained from ATCC. The cell inoculum for each cell line was prepared by treating stock cultures with 5.0 ml of a solution of Trypsin/EDTA (ethylenediamine tetraacetate) (GIBCO/BRL) and suspending the single cells in the reconstituted culture medium of Example I (pH 7.2) supplemented with Protein Supplement A. The cells of each cell line then were added to triplicate T-25 flasks containing the reconstituted culture medium supplemented with fetal bovine serum at the concentrations shown in Table V. The flasks were sealed and placed in a 37° C. incubator.

After five days of culture, the medium was removed from each flask, and the cultures were treated with Trypsin/EDTA solution as above. After the cells had detached from the surface of the flask, they were resuspended in a phosphate buffered saline solution. The cell number was determined with a Coulter Counter (TM) particle counter (Coulter Electronics). The results are shown in Table V.

TABLE V

| Cell Line | Serum | Cells per Flask Initial | Day 5 |
|---|---|---|---|
| CL 101 | 1% | $9.5 \times 10^4$ | $11.4 \pm .4 \times 10^5$ |
| CCL 209 | 2% | $1.0 \times 10^4$ | $3.3 \pm .2 \times 10^4$ |

EXAMPLE VII

The medium of this invention was used for the production of monoclonal antibodies in an Amicon Vitafiber II-P30 (TM) (Amicon Division of W. R. Grace & Co.-Conn.) hollow fiber bioreactor (nominal ultrafiltrative cut-off of 30,000 MW). The system was constructed to permit exchange of fresh medium with the medium that was continuously recirculated through the hollow fiber cartridge. The rate of this exchange was increased as the cartridge filled with cultured cells. The final exchange rate (for the filled cartridge) was approximately 2.0 L/day, and 81.0 L of medium were used during the entire bioreactor run.

Following sterilization and assembly, the hollow fiber cartridge and bioreactor system were sequentially flushed with tissue culture grade water and with the reconstituted medium of Example I (pH 7.2). The medium-contacting surfaces of the system were coated with protein via incubation with the medium of this invention, reconstituted from the powder of Example I by the reconstitution procedure described (pH 7.2) with the following protein supplement 1.0 mg/ml BSA, 1.0 $\mu$gm/ml TF, and 5.0 $\mu$gm/ml INS. The sterility of the system was verified by visual observation of medium clarity after operation for three days with this medium.

The cartridge was then inoculated with three hundred million CRL 1606 cells Daily samples were taken and measured for pH. Each time the pH dropped below 6.8, the medium feed rate was increased, up to a maximum of 2.0 L/day. When that rate was reached, the medium was switched to an identical medium reconstituted at pH 7.35.

Samples were taken from the cell space as indicated in Table VI, and the monoclonal antibody product (MAB) was characterized and quantified by HPSEC as in Example IV. In most of the samples, the purity of the MAB was greater than 95%. The cumulative production of MAB by this hollow fiber bioreactor over 49 days of operation with the medium of this invention is shown in Table VI.

TABLE VI

| Total Days of Operation | Cumulative Production (gm) |
|---|---|
| 7 | 0.006 |
| 10 | 0.022 |
| 14 | 0.370 |
| 18 | 1.441 |
| 21 | 2.202 |
| 24 | 2.570 |
| 28 | 2.852 |
| 36 | 3.458 |
| 39 | 3.847 |
| 44 | 4.299 |
| 48 | 4.662 |

Similar results were obtained using other hollow fiber bioreactors constructed with other fibers having 10,000 and 30,000 MW nominal ultrafiltrative cut-offs.

EXAMPLE VIII

This example demonstrates the ability of various zwitterionic buffers to function in the media of the invention. Five media containing various zwitterionic buffers were tested.

The media of this example are based on the medium of Example I, and are supplemented with 10 $\mu$g/ml insulin and 10 $\mu$g/ml transferrin Duplicate 200 ml roller bottles were seeded at $2 \times 10^4$ CRL 1606 cells per milliliter of medium for each medium tested. The first medium was the medium of Example I, which contained 25 mM HEPES. The other media differ based on zwitterionic buffer conditions. Media 2-5 contain 25 mM MOPSO, 25 mM BES, 12.5 mM HEPES and 12.5 mM MOPSO, and 12.5 mM HEPES and 12.5 mM BES, respectively.

Cells were counted on days 3-6 Cell growth was observed in all conditions; numbers of viable cells are indicated in Table VII. Antibody titer from day 7 culture were determined by HPSEC and are shown in Table VII.

TABLE VII

| Buffer | Viable Cells ($\times 10^4$) Day: 3 | 4 | 5 | 6 | Antibody $\mu$g/ml |
|---|---|---|---|---|---|
| 25 mM HEPES | 34 | 91 | 180 | 240 | 204.5 |
| 25 mM MOPSO | 25 | 76 | 180 | 220 | 162.0 |
| 25 mM BES | 26 | 81 | 180 | 240 | 154.5 |
| 12.5 mM HEPES; 12.5 mM | 27 | 88 | 185 | 225 | 196.5 |

TABLE VII-continued

| Buffer | Viable Cells ($\times 10^4$) Day: 3 | 4 | 5 | 6 | Antibody µg/ml |
|---|---|---|---|---|---|
| MOPSO 12.5 mM HEPES; 12.5 mM BES | 41 | 125 | 210 | 245 | 226.5 |

These results indicate that various zwitterionic buffers can be used in an equally effective manner.

Example IX

This example demonstrates the use of the various zwitterionic buffers of the media of the invention to promote in situ weaning, growth, and antibody production of cells in a high density hollow fiber bioreactor.

A Vitafiber VF 3700 bioreactor (Amicon Division of W. R. Grace & Co.-Conn.) was inoculated with HB 55 cells. HB 55 cells are a hybridoma line obtained from the American Type Culture Collection. The HB 55 cells could not be weaned below 2% FBS (fetal bovine serum) in roller bottles $10^9$ cells were pumped into the extracapillary space with 800 ml of conditioned medium and immediately attached to two stack packs (10 L blood bags filled with medium). The bottom stack pack contained the HEPES containing media of Example VIII supplemented with 1% FBS; the top stack pack contained the same medium without serum. Once both bags were exhausted, only serum free medium was attached. The cells were successfully weaned by this procedure and were producing antibody maximally by day 13. Between measurements made on days 14 and 15, the feed pump was off for 12-18 hours (cause unknown) While the cell population suffered some damage, it recovered over the next several days.

During its 82 day operation, the bioreactor produced over 17 gm of antibody (by RID analysis, or well over 20 gm by HPSEC.) at a fairly constant rate of 230-300 mg/day (by RID, or 280-340 mg/day by HPSEC.) The media described in Example VIII were attached as noted in Table VIII, and the medium feed rate was held constant at just under 3 L/day during this time. The amount of antibody produced as measured by RID or HPSEC by each medium is also given in Table VIII.

TABLE VIII

| Days | Buffer System | Antibody (mg/day) RID | HPSEC |
|---|---|---|---|
| 19-23 | 25 mM HEPES | 232.5 | 304.4 |
| 24-33 | 25 mM BES | 262.5 | 286.3 |
| 34-43 | 12.5 mM HEPES, 12.5 mM BES | 306.9 | 349.1 |
| 44-53 | 25 mM MOPSO | 263.3 | 315.0 |
| 54-62 | 12.5 mM HEPES, 12.5 mM MOPSO | 256.7 | 297.7 |
| 63-82 | 25 mM HEPES | 246.4 | 298.4 |

The best performing buffer system of those tried was 12.5 mM HEPES/12.5 mM BES; however, the differences between buffer systems are small. Interestingly, this result agrees with results of Example VIII where CRL 1606 cells were grown in roller bottles and maximal antibody production was observed in the medium buffered with 12.5 mM HEPES/12.5 mM BES.

Example X

This example demonstrates the ability of inorganic iron compounds to replace transferrin as a defined protein supplements.

CRL 1606 cells were innoculated at day 0 into 200 ml roller bottles containing the test medium and incubated at 37° C. at 1.5 rpm. Basic medium A (BMA) was the unsupplemented medium of Example I supplemented with 50 µgm/ml bovine serum albumin, and 5 µgm/ml insulin Basic medium B (BMB) was BMA plus 50 µM monothioglycerol. Basic medium C. (BMC.) was BMA plus iron chelator DFO. The test media were the different basic media supplemented with either 5 µgm/ml transferrin (TF), 50 µM ferric sulfate ($Fe_2(SO_4)_3$), 50 µM ferrous sulfate ($FeSO_4$), or 50 µM ferric citrate ($FeC_6H_5O_7$). The results of these experiments are shown in Table IX.

TABLE IX

| Medium | Cell Number ($\times 10^4$) Day | | | | | | | Antibody Produced (ng/L) Day | | | |
|---|---|---|---|---|---|---|---|---|---|---|---|
| | 0 | 3 | 4 | 5 | 6 | 7 | 8 | 4 | 5 | 6 | 7 |
| BMB + TF | 2 | | 13 | 31 | 58 | 72 | | | 0 | 48 | 82 |
| BMB + $Fe_2(SO_4)_3$ | 2 | | 19 | 59 | 100 | 120 | | | 29 | 74 | 90 |
| BMA + TF | 2 | 17 | 55 | 110 | | | | | | | |
| BMA + $Fe_2(SO_4)_3$ | 2 | 20 | 66 | 122 | | | | | | | |
| BMA + $FeSO_4$ | 2 | 2 | 2 | 2 | | | | | | | |
| BMC | | | | | | | | | 2 | 20 | 22 |
| BMC + TF | | | | 173 | 255 | 262 | 267 | 48 | | 96 | 231 |
| BMC + $FeC_6H_5O_7$ | | | | 80 | 171 | 228 | 254 | 32 | | 98 | 227 |
| BMC + $Fe_2(SO_4)_3$ | | | | 126 | 213 | 247 | 226 | | | | |

The results of Table IX indicate that both ferric sulfate and ferric citrate can substitute for transferrin as iron sources.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

TABLE 1

| COMPONENT | MW | M | mg/L |
|---|---|---|---|
| Carbohydrates and Derivatives | | | |
| D-Glucose | 180.16 | $2 \times 10^{-2}$ | 3603.2 |
| Na Pyruvate | 110.0 | $1 \times 10^{-3}$ | 110.0 |
| Bulk Ions & Trace Elements | | | |
| $CaCl_2 \cdot 2H_2O$ | 147.02 | $1 \times 10^{-3}$ | 147.02 |
| $CuSO_4 \cdot 5H_2O$ | 249.68 | $3 \times 10^{-9}$ | 0.000749 |
| $FeSO_4 \cdot 7H_2O$ | 278.02 | $1 \times 10^{-6}$ | 0.278 |

TABLE 1-continued

| COMPONENT | MW | M | mg/L |
|---|---|---|---|
| Fe(NO$_3$)$_3$.9H$_2$O | 404.02 | 2 × 10$^{-7}$ | 0.0808 |
| KCl | 74.55 | 4 × 10$^{-3}$ | 298.2 |
| MgSO$_4$.7H$_2$O | 246.38 | 8 × 10$^{-4}$ | 197.1 |
| NaCl | 58.44 | 1.05 × 10$^{-1}$ | 6136.2 |
| Na$_2$HPO$_4$.7H$_2$O | 268.1 | 3 × 10$^{-4}$ | 80.43 |
| NaH$_2$PO$_4$.2H$_2$O | 156.01 | 6 × 10$^{-4}$ | 93.606 |
| Na$_2$SeO$_3$.5H$_2$O | 263.01 | 3 × 10$^{-8}$ | 0.00789 |
| Na$_2$SiO$_3$.9H$_2$O | 284.2 | 1 × 10$^{-5}$ | 2.842 |
| (NH$_4$)$_6$Mo$_7$O$_{24}$.4H$_2$O | 1235.9 | 3 × 10$^{-9}$ | 0.00371 |
| NH$_4$VO$_3$ | 116.99 | 5 × 10$^{-10}$ | 0.0000585 |
| NiSO$_4$.6H$_2$O | 262.80 | 3 × 10$^{-10}$ | 0.0000788 |
| ZnSO$_4$.7H$_2$O | 287.54 | 8 × 10$^{-7}$ | 0.23 |
| Amino Acids | | | |
| L-Arg | 210.7 | 8 × 10$^{-4}$ | 168.56 |
| L-Cys HCl.H$_2$O | 175.6 | 3 × 10$^{-4}$ | 52.68 |
| L-Gln | 146.1 | 5 × 10$^{-3}$ | 730.5 |
| L-His HCl.H$_2$O | 209.7 | 2 × 10$^{-4}$ | 41.94 |
| L-Hydroxy-Pro | 131.13 | 1 × 10$^{-4}$ | 13.113 |
| L-Ile | 131.2 | 6 × 10$^{-4}$ | 78.72 |
| L-Leu | 131.2 | 6 × 10$^{-4}$ | 78.72 |
| L-Lys HCl | 182.7 | 8 × 10$^{-4}$ | 146.16 |
| L-Met | 149.2 | 1 × 10$^{-3}$ | 149.2 |
| L-Phe | 165.2 | 3 × 10$^{-4}$ | 49.56 |
| L-Thr | 119.1 | 6 × 10$^{-4}$ | 71.46 |
| L-Trp | 204.2 | 6 × 10$^{-5}$ | 12.252 |
| L-Tyr (diNa$^+$)2H$_2$O | 263.2 | 3 × 10$^{-4}$ | 78.95 |
| L-Val | 117.2 | 6 × 10$^{-4}$ | 70.32 |
| L-Ala | 89.09 | 2 × 10$^{-5}$ | 1.782 |
| L-Asn.H$_2$O | 150.1 | 3 × 10$^{-4}$ | 45.03 |
| L-Asp | 133.1 | 2 × 10$^{-5}$ | 2.662 |
| L-Glu | 147.1 | 2 × 10$^{-5}$ | 2.942 |
| Gly | 75.07 | 3 × 10$^{-5}$ | 2.252 |
| L-Pro | 115.1 | 2 × 10$^{-4}$ | 23.02 |
| L-Ser | 105.1 | 3 × 10$^{-4}$ | 31.53 |
| Amino Acid Derivatives | | | |
| Glutathione | 307.3 | 1 × 10$^{-6}$ | 0.307 |
| Putrescine 2HCl | 161.1 | 3 × 10$^{-7}$ | 0.048 |
| Water Soluble Vitamins and Co-Enzyme | | | |
| Biotin | 244.3 | 3 × 10$^{-8}$ | 0.007 |
| D-Ca pantothenate | 238.3 | 2 × 10$^{-5}$ | 4.766 |
| Folic acid | 441.41 | 6 × 10$^{-6}$ | 2.648 |
| Folinic acid (Ca$^+$) 5H$_2$O | 601.6 | 1 × 10$^{-6}$ | 0.602 |
| Niacinamide (Nicotinamide) | 122.1 | 3 × 10$^{-5}$ | 3.663 |
| p-Aminobenzoic acid | 137.14 | 3 × 10$^{-6}$ | 0.411 |
| Pyridoxal HCl | 203.6 | 1 × 10$^{-5}$ | 2.036 |
| Pyridoxine HCl | 205.6 | 3 × 10$^{-7}$ | 0.062 |
| Riboflavin | 376.4 | 8 × 10$^{-7}$ | 0.301 |
| Thiamine HCl | 337.0 | 9 × 10$^{-6}$ | 3.036 |
| Vitamin B12 | 1355.4 | 3 × 10$^{-7}$ | 0.407 |
| Nucleic Acid Derivatives | | | |
| Adenine | 135.13 | 1 × 10$^{-6}$ | 0.135 |
| Hypoxanthine (Na$^+$) | 146.1 | 7 × 10$^{-6}$ | 1.0227 |
| Thymidine HCl | 337.3 | 1 × 10$^{-5}$ | 3.373 |
| Lipids and Derivatives | | | |
| Choline chloride | 139.63 | 1 × 10$^{-4}$ | 13.96 |
| Ethanolamine HCl | 97.55 | 2 × 10$^{-5}$ | 1.951 |
| i-Inositol | 180.2 | 1 × 10$^{-4}$ | 18.02 |
| Linoleic acid | 280.4 | 1 × 10$^{-7}$ | 0.028 |
| Lipoic acid | 206.3 | 2 × 10$^{-7}$ | 0.041 |
| Buffers | | | |
| Zwitterionic Buffer* | | 2.5 × 10$^{-2}$ | |
| NaOH | 40.01 | 1.23 × 10$^{-2}$ | 492.12 |
| NaHCO$_3$ | 84.01 | 3 × 10$^{-3}$ | 252.03 |
| mM sodium (total) | 123.1 | | |
| mM potassium (total) | 4.0 | | |
| sodium:potassium | 30.7 | | |
| total osmolarity (mosm) | 302.7 | | |

*The zwitterionic buffer can be one or a combination of more than one suitable zwitterionic buffers. Therefore, the MW and mg/l is dependent upon the particular buffer used.

What is claimed is:

1. An air-equilibrated basal nutrient medium for in vitro mammalian cell culture, consisting essentially of the following:

| | |
|---|---|
| D-Glucose | 2 × 10$^{-2}$M |
| Na Pyruvate | 1 × 10$^{-3}$M |
| CaCl$_2$.2H$_2$O | 1 × 10$^{-3}$M |
| CuSO$_4$.5H$_2$O | 3 × 10$^{-9}$M |
| FeSO$_4$.7H$_2$O | 1 × 10$^{-6}$M |
| Fe(NO$_3$)$_3$.9H$_2$O | 2 × 10$^{-7}$M |
| KCl | 4 × 10$^{-3}$M |
| MgSO$_4$.7H$_2$O | 8 × 10$^{-4}$M |
| NaCl | 1.05 × 10$^{-1}$M |
| Na$_2$HPO$_4$.7H$_2$O | 3 × 10$^{-4}$M |
| NaH$_2$PO$_4$.2H$_2$O | 6 × 10$^{-4}$M |
| Na$_2$SeO$_3$.5H$_2$O | 3 × 10$^{-8}$M |
| Na$_2$SiO$_3$.9H$_2$O | 1 × 10$^{-5}$M |
| (NH$_4$)$_6$Mo$_7$O$_{24}$.4H$_2$O | 3 × 10$^{-9}$M |
| NH$_4$VO$_3$ | 5 × 10$^{-10}$M |
| NiSO$_4$.6H$_2$O | 3 × 10$^{-10}$M |
| ZnSO$_4$.7H$_2$O | 8 × 10$^{-7}$M |
| L-Arg | 8 × 10$^{-4}$M |
| L-Cys HCl.H$_2$O | 3 × 10$^{-4}$M |
| L-Gln | 5 × 10$^{-5}$M |
| L-His HCl.H$_2$O | 2 × 10$^{-4}$M |
| L-Hydroxy-Pro | 1 × 10$^{-4}$M |
| L-Ile | 6 × 10$^{-4}$M |
| L-Leu | 6 × 10$^{-4}$M |
| L-Lys HCl | 8 × 10$^{-4}$M |
| L-Met | 1 × 10$^{-3}$M |
| L-Phe | 3 × 10$^{-4}$M |
| L-Thr | 6 × 10$^{-4}$M |
| L-Trp | 6 × 10$^{-5}$M |
| L-Tyr (diNa$^+$)2H$_2$O | 3 × 10$^{-4}$M |
| L-Val | 6 × 10$^{-4}$M |
| L-Ala | 2 × 10$^{-5}$M |
| L-Asn.H$_2$O | 3 × 10$^{-4}$M |
| L-Asp | 2 × 10$^{-5}$M |
| L-Glu | 2 × 10$^{-5}$M |
| Gly | 3 × 10$^{-5}$M |
| L-Pro | 2 × 10$^{-4}$M |
| L-Ser | 3 × 10$^{-4}$M |
| Glutathione | 1 × 10$^{-6}$M |
| Putrescine 2HCl | 3 × 10$^{-7}$M |
| Biotin | 3 × 10$^{-8}$M |
| D-Ca pantothenate | 2 × 10$^{-5}$M |
| Folic acid | 6 × 10$^{-6}$M |
| Folinic acid (Ca$^+$).5H$_2$O | 1 × 10$^{-6}$M |
| Niacinamide (Nicotinamide) | 3 × 10$^{-5}$M |
| p-Aminobenzoic acid | 3 × 10$^{-6}$M |
| Pyridoxal HCl | 1 × 10$^{-5}$M |
| Pyridoxine HCl | 3 × 10$^{-7}$M |
| Riboflavin | 8 × 10$^{-7}$M |
| Thiamine HCl | 9 × 10$^{-6}$M |
| Vitamin B12 | 3 × 10$^{-7}$M |
| Adenine | 1 × 10$^{-6}$M |
| Hypoxanthine (Na$^+$) | 7 × 10$^{-6}$M |
| Thymidine HCl | 1 × 10$^{-5}$M |
| Choline chloride | 1 × 10$^{-4}$M |
| Ethanolamine HCl | 2 × 10$^{-5}$M |
| i-Inositol | 1 × 10$^{-4}$M |
| Linoleic acid | 1 × 10$^{-7}$M |
| Lipoic acid | 2 × 10$^{-7}$M |
| Zwitterionic Buffer | 2.5 × 10$^{-2}$M |
| NaOH | 1.23 × 10$^{-2}$M |
| NaHCO$_3$ | 3 × 10$^{-3}$M |

2. The nutrient medium of claim 1 wherein the zwitterionic buffer is selected from the group consisting of HEPES, MOPSO, BES, TAPSO and a combination thereof.

3. The nutrient medium of claim 1 which is supplemented with an inorganic iron source, and defined proteins, or a combination thereof.

4. The nutrient medium of claim 3 wherein said inorganic iron source is selected from the group consisting of ferric sulfate, ferric citrate, ferrous fumarate and ferrous ammonium sulfate.

5. The nutrient medium of claim 3 wherein said defined proteins are selected from the group consisting of albumin, insulin and iron-saturated transferrin.

6. The nutrient medium of claim 1 which has an osmolarity of about 285 to about 315 milli-osmols.

7. The nutrient medium of claim 6 which has an osmolarity of about 295 to about 305 milli-osmols.

8. The nutrient medium of claim 1 which has a pH of about 7.0 to about 8.0.

9. The nutrient medium of claim 8 which has a pH of about 7.2.

10. The nutrient medium of claim 8 which has a pH of about 7.35 to about 7.8.

11. The nutrient medium of claim 11 which has a sodium-to-potassium ratio of about 25 to about 35.

12. The nutrient medium of claim 11 in which said ratio is about 30.

13. The nutrient medium of claim 1 wherein the nutrient medium is supplemented with serum or another biological extract.

14. The nutrient medium of claim 13 in which said serum or extract is less than about one percent of the medium by volume.

* * * * *